United States Patent
Gupta et al.

(10) Patent No.: US 8,588,495 B2
(45) Date of Patent: Nov. 19, 2013

(54) SYSTEMS AND METHODS FOR COMPUTER AIDED DIAGNOSIS AND DECISION SUPPORT IN WHOLE-BODY IMAGING

(75) Inventors: Alok Gupta, Bryn Mawr, PA (US); Arun Krishnan, Exton, PA (US); Xiang Sean Zhou, Exton, PA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 0 days.

(21) Appl. No.: 12/968,492

(22) Filed: Dec. 15, 2010

(65) Prior Publication Data

US 2011/0142320 A1    Jun. 16, 2011

Related U.S. Application Data

(62) Division of application No. 11/505,081, filed on Aug. 16, 2006, now abandoned.

(60) Provisional application No. 60/721,457, filed on Sep. 28, 2005.

(51) Int. Cl.
*G06K 9/00* (2006.01)
*A61B 5/00* (2006.01)
*A61B 5/05* (2006.01)
*G06Q 10/00* (2012.01)

(52) U.S. Cl.
USPC ........... 382/131; 382/128; 382/129; 382/130; 382/132; 600/300; 600/427; 705/2

(58) Field of Classification Search
USPC ............... 382/128–132; 600/300, 427; 705/2
See application file for complete search history.

(56) References Cited

U.S. PATENT DOCUMENTS

| | | | |
|---|---|---|---|
| 5,920,319 A * | 7/1999 | Vining et al. | 345/420 |
| 7,668,351 B1 * | 2/2010 | Soliz et al. | 382/128 |
| 2002/0156364 A1* | 10/2002 | Madore | 600/410 |
| 2002/0172403 A1* | 11/2002 | Doi et al. | 382/128 |
| 2004/0030246 A1* | 2/2004 | Townsend et al. | 600/427 |
| 2004/0078753 A1* | 4/2004 | Doyle | 715/501.1 |
| 2004/0097805 A1* | 5/2004 | Verard et al. | 600/428 |
| 2005/0010445 A1* | 1/2005 | Krishnan et al. | 705/2 |
| 2005/0021375 A1* | 1/2005 | Shimizu et al. | 705/2 |
| 2005/0088177 A1* | 4/2005 | Schreck et al. | 324/307 |
| 2005/0129295 A1* | 6/2005 | Shanmugam et al. | 382/131 |
| 2007/0019846 A1* | 1/2007 | Bullitt et al. | 382/128 |

* cited by examiner

*Primary Examiner* — Amara Abdi
(74) *Attorney, Agent, or Firm* — Peter R. Withstandley

(57) ABSTRACT

A system for providing automatic diagnosis and decision support includes: a medical image database; generative learning and modeling modules that build distributional appearance models and spatial relational models of organs or structures using images from the medical image database; a statistical whole-body atlas that includes one or more distributional appearance models and spatial relational models of organs or structure, in one or more whole-body imaging modalities, built by the generative learning and modeling modules; and discriminative learning and modeling modules that build two-class or multi-class classifiers for performing at least one of organ, structure or disease detection or segmentation.

16 Claims, 4 Drawing Sheets

SYSTEMS AND METHODS FOR COMPUTER AIDED DIAGNOSIS AND DECISION SUPPORT IN WHOLE-BODY IMAGING

CROSS-REFERENCE TO RELATED PATENT APPLICATION

This application claims the benefit of U.S. Provisional Application Ser. No. 60/721,457, filed Sep. 28, 2005 entitled "Method and Apparatus for Computer Aided Diagnosis and Therapy Decision Support in Whole Body Imaging" and U.S. patent application Ser. No. 11/505,081 entitled Systems and Methods for Computer Aided Diagnosis and Decision Support in Whole-Body Imaging, the content of which are herein incorporated by reference in their entirety.

BACKGROUND OF THE INVENTION

1. Technical Field

The present disclosure relates to systems and methods for providing automated diagnosis and decision support in medical imaging and, more particularly, to systems and methods for providing automated diagnosis and decision support in whole-body imaging.

2. Discussion of Related Art

Medical imaging is generally recognized as important for diagnosis and patient care. In recent years, medical imaging has experienced an explosive growth due to advances in imaging modalities such as x-rays, computed tomography (CT), magnetic resonance imaging (MRI) and ultrasound. Many existing and emerging whole-body imaging modalities are showing great potential for supporting new or improved pre-clinical and clinical applications and workflows. These modalities include whole-body MRI, positron emission tomography (PET), single-photon emission computed tomography (SPECT), PET/CT, SPECT/CT, whole-body CT (MDCT), and PET/MR.

Whole-body imaging modalities can be useful for non-organ-specific oncologic staging. For example, studies have shown that whole-body PET and whole-body MRI are more sensitive and specific than traditional skeletal scintigraphy in the assessment of metastatic bone disease. In general, whole-body PET can identify the extent and severity of disease more accurately than CT, MR or other imaging modalities. PET can be useful for detecting disease before it has grown to a detectable size for CT or MR.

Challenges in whole-body imaging include the increased data volume, anatomical or functional variability throughout the body, breathing/motion artifacts and joint articulations, and the possibly lower spatial resolution as compared to focused organ/sectional scans. For example, a whole-body scan yields a large data volume which requires more reading time. In a non-organ-specific whole-body scan, the reader such as a physician, a radiologist, or a technologist, may not know precisely what to look for or at what location, or how to differentiate normal versus abnormal, that is, physiological versus pathological uptakes in PET. In many cases, whole-body screening has less spatial resolution than a focused image study of a particular organ. Non-rigid image matching or registration is difficult for sectional/organ images such as images of the brain or the lungs, and it becomes even more difficult for whole-body scans, because of the additional articulated motion of body parts. Qualitative changes may be easier to see, but quantitative changes over time are difficult to report, particularly when accurate deformable whole-body matching is not readily achievable.

There is a vast amount of literature relating to the topics of computer aided detection, diagnosis, and decision support for medical imaging applications. Most of these are organ-specific, focusing on one of breast, brain, heart, lung, colon, etc. Image analysis applications that employ active shape models, active motion models and active appearance models generally use over-simplified statistical assumptions such as the Gaussian assumption. Existing solutions for image segmentation and registration rely on predefined procedures, such as first edge/corner detection and Hough transform, or other hand-crafted features that are not readily scalable or adaptable to changing patient sample bases, evolving disease statistics, or ever-advancing hardware technologies.

SUMMARY OF THE INVENTION

According to an exemplary embodiment of the present invention, a system for providing automatic diagnosis and decision support includes: a medical image database; generative learning and modeling modules that build distributional appearance models and spatial relational models of organs or structures using images from the medical image database; a statistical whole-body atlas that includes one or more distributional appearance models and spatial relational models of organs or structure, in one or more whole-body imaging modalities, built by the generative learning and modeling modules; and discriminative learning and modeling modules that build two-class or multi-class classifiers for performing at least one of organ, structure, or disease detection or segmentation.

According to an exemplary embodiment of the present invention, a method is provided for providing automatic diagnosis and decision support in whole-body imaging. The method includes: using whole-body imaging to obtain a first set of image data of a patient; fitting a statistical whole-body atlas using the first set of image data, wherein the statistical whole-body atlas includes at least one of statistics on voxel intensities, statistics on global and local shape deformations, or statistics on joint articulations; and using the statistical whole-body atlas to characterize pathological findings in terms of a diagnosis.

According to an exemplary embodiment of the present invention, a method is provided for providing automatic diagnosis and decision support in whole-body imaging. The method includes: detecting and segmenting one or more selected regions of interest in whole-body images; detecting one or more abnormalities by automatically interpreting whole-body images of the selected regions of interest for pathological findings; and characterizing the pathological findings in terms of a diagnosis.

According to an exemplary embodiment of the present invention, there is provided a program storage device readable by machine, tangibly embodying a program of instructions executable by the machine to perform method steps for providing automatic diagnosis and decision support, the method steps comprising:

using whole-body imaging to obtain a first set of image data of a patient; fitting a statistical whole-body atlas using the first set of image data, wherein the statistical whole-body atlas includes at least one of statistics on voxel intensities, statistics on global and local shape deformations, or statistics on joint articulations; and using the statistical whole-body atlas to characterize pathological findings in terms of a diagnosis.

According to an exemplary embodiment of the present invention, there is provided a program storage device readable by machine, tangibly embodying a program of instructions executable by the machine to perform method steps for providing automatic diagnosis and decision support, the method steps comprising: detecting and segmenting one or more selected regions of interest in whole-body images; detecting one or more abnormalities by automatically interpreting whole-body images of the selected regions of interest for pathological findings; and characterizing the pathological findings in terms of a diagnosis.

BRIEF DESCRIPTION OF THE DRAWINGS

The present invention will become more apparent to those of ordinary skill in the art when descriptions of exemplary embodiments thereof are read with reference to the accompanying drawings.

DESCRIPTION OF EXEMPLARY EMBODIMENTS

Hereinafter, exemplary embodiments of the present invention will be described in detail with reference to the accompanying drawings.

In exemplary embodiments of the present invention, systems and methods for providing automatic diagnosis and decision support in whole-body imaging use advanced image analysis tools and machine intelligence to aid the image reading process with automatic anatomical and functional interpretation, automatic pathology detection and disease diagnosis. In exemplary embodiments of the present invention, systems and methods for providing automatic diagnosis and decision support in whole-body imaging enhance current workflow with accurate disease characterization, change quantification, progression monitoring, disease management and speed up clinical workflow.

Figure 1:
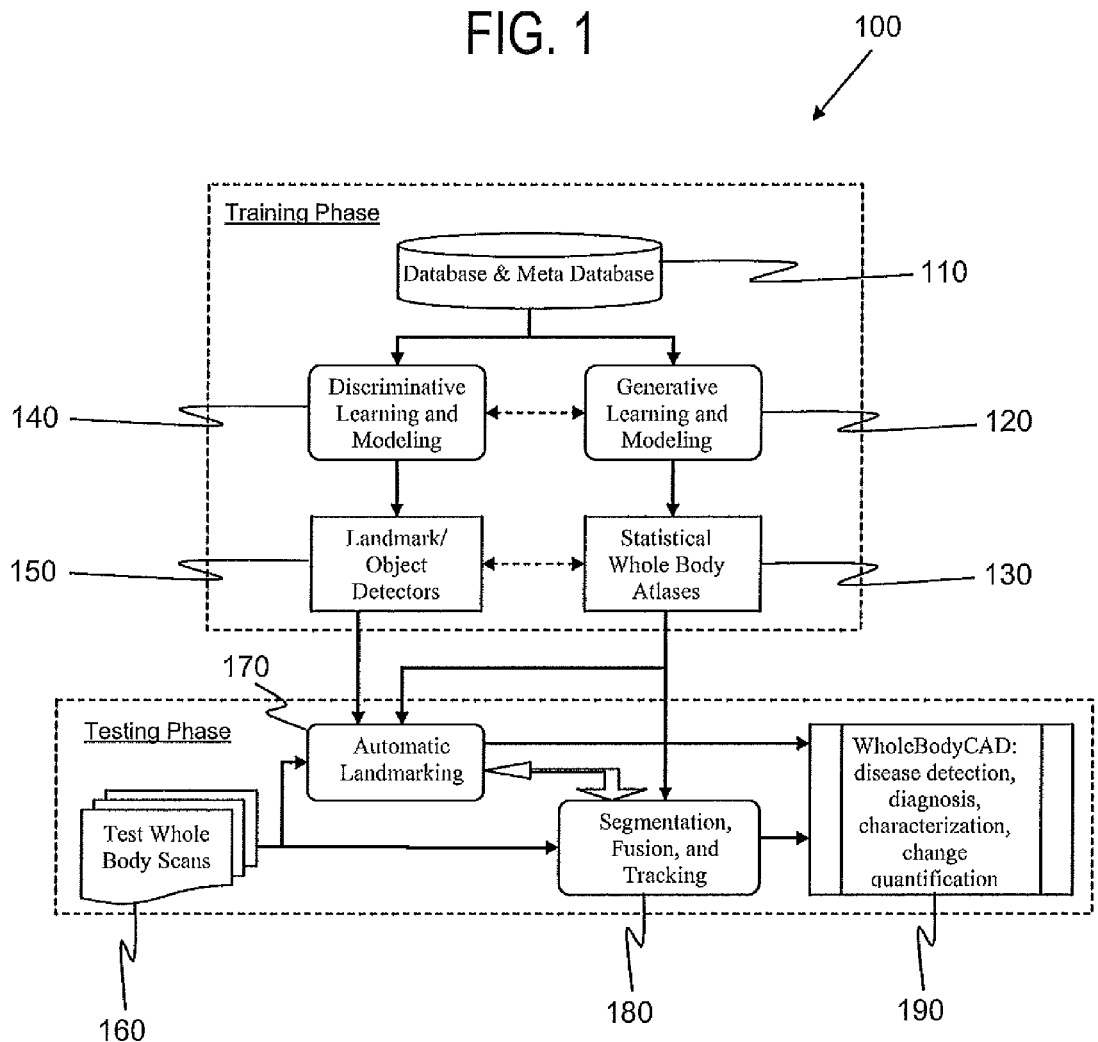
FIG. 1 illustrates a learning-based and database-guided framework to support automatic diagnosis and decision support in whole-body imaging, according to an exemplary embodiment of the present invention.

FIG. 1 illustrates a learning-based and database-guided framework to support automatic diagnosis and decision support in whole-body imaging, according to an exemplary embodiment of the present invention. Referring to FIG. 1, the learning-based and database-guided framework 100 includes a training phase and a testing phase as indicated by the dashed boxes.

The training phase shown in FIG. 1 includes a database 110 with associated meta data, generative learning and modeling 120, a statistical whole body atlas 130, discriminative learning and modeling 140, and landmark/object detectors 150.

The database 110 with associated meta data may comprise a medical image database. Examples of images include positron emission tomography (PET) images, computed tomography (CT) images, magnetic resonance imaging (MRI) images, single-photon emission computed tomography (SPECT) images, etc. Examples of meta data include annotation of organs; annotations of pathological findings, for example, by a location vector, or by lines, curves and/or surfaces; and additional information associated with the images, such as for example, patient demographics, clinical history, etc.

Generative learning and modeling 120 is based on annotated training data and can extract statistics, find clusters, and build distributional appearance models or spatial relational models of organs or structures, or spatial or conceptual dependency models for diseases.

The statistical whole body atlas 130 may comprise mathematical appearance and/or spatial models of organs or structures in one or multiple whole body imaging modalities. Each model may comprise one or more organs, along with their appearances models and a distributional model to capture their relative locations.

Discriminative learning and modeling 140 is based on annotated training data and can formulate the problem of organ detection/segmentation as a discriminative learning problem, design/select discriminative features, and build two-class or multi-class learning machines, such as classifiers.

Landmark/object detectors 150 may comprise software modules, which can take whole body images as input, and output the location of one or multiple landmark points, for example, an upper corner of the left or right lung or the center of the left or right kidney, etc., and the location of one or more organs.

The testing phase shown in FIG. 1 includes whole body scans/images 160 to be analyzed by the system, automatic landmarking 170, segmentation, fusion and tracking 180, and whole-body CAD 190.

The automatic landmarking 170 uses both the landmark/object detectors 150 and the statistical whole body atlas 130. The output of this module is an annotated "map" of the whole-body images, with multiple organs localized jointly, based on initial detection of the detector module, and verification by the statistical whole body atlas 130. This module combines the results from the landmark/object detectors 150, statistical whole body atlas 130 and the automatic landmarking 170, and outputs the segmentation, for example, in the forms of a bounding box, a bounding surface, and/or a segmentation mask, of the detected/localized organs.

In whole-body CAD 190, the results of the automatic landmarking 170 and segmentation, fusion and tracking 180 are used to support any of the following: disease detection in each organ of interest, for example, by comparison with the normal appearance, shape, and location of an organ encoded in the statistical whole body atlas 130; diagnosis, for example, by comparison with different models of the detected disease; characterization, such as for example, size, type, stage, etc.; and change quantification across time points.

In an exemplary embodiment of the present invention, a system for providing automatic diagnosis and decision support in whole-body imaging includes a medical image database, generative learning and modeling modules, a statistical whole-body atlas and discriminative learning and modeling modules. The medical image database comprises 2-D image data, 3-D image data and/or higher-dimensional image data.

The generative learning and modeling modules build distributional appearance models and spatial relational models of organs or structures using images from the medical image database.

The statistical whole-body atlas includes one or more distributional appearance models and spatial relational models of organs or structure, in one or more whole-body imaging modalities, built by the generative learning and modeling modules. For each given modality, such as for example, PET, CT, or MR, a statistical whole-body atlas contains one or more 3D canonical whole body scans, each with associated statistics on voxel intensities, statistics on global and local shape deformations, and statistics on joint articulations. Each canonical whole body scan can be the average of multiple scans from a database that are rigidly and/or non-rigidly aligned by organs and body structures.

The associated statistics on voxel intensities can be a non-parametric or parametric representation of the underlying database. As a special case, if we represent the distribution as a Gaussian, the associated statistics on voxel intensities can stored in the form of a whole body scan, with each voxel coding the variance of the distribution. The statistics on global and local shape deformations can be represented as deformation fields, or as search ranges (in X, Y, and Z directions) coded at each voxel location. This can be learned from ground truth annotations in the form of landmark points, lines, curves, or surfaces.

The statistical whole-body atlas is statistical in the sense that it encodes variations in the database in terms of appearance, deformations, and articulations. The statistics on joint articulations can be represented in a table, recording either the distributions of each joint articulation in the database, the means and variances of articulations, or simply the range of articulations.

The statistical atlas is a form of descriptive or generative modeling of the database. It encodes anatomical or functional variations of the whole body or body parts (either physiological or pathological). The statistical whole-body atlas may include models and priors for both generative and discriminative learning in later stages. The statistical whole-body atlas comprises one or more three-dimensional canonical whole-body scans, each with associated statistics on voxel intensities, statistics on global and local shape deformations, and statistics on joint articulations.

The discriminative learning and modeling modules according to an exemplary embodiment of the present invention build two-class or multi-class classifiers for performing at least one of organ or structure detection or segmentation. The generative learning and modeling modules may extract statistics and find clusters using images from the medical image database. The statistics comprise at least one of statistics on voxel intensities, statistics on global and local shape deformations, or statistics on joint articulations. The discriminative learning and modeling modules may formulate organ detection and segmentation as discriminative learning and at least one of design or select discriminative features.

In an exemplary embodiment of the present invention, a system for providing automatic diagnosis and decision support in whole-body imaging further includes software modules to output a location of one or more landmark points and/or a location of more or more organs, using one or more images from the medical image database. For example, landmark points may comprise an upper corner of a left lung, an upper corner of a right lung, a tip of a left kidney or a tip of a right kidney. Automatic landmarking, in accordance with an exemplary embodiment of the present invention, comprises discriminative learning and modeling of local appearance and shape. Discriminative techniques, including but not limited to, Boosting, AdaBoosting, Support Vector Machines and Decision Trees may be used for the modeling, detection, and localization of whole-body landmarks.

Figure 2:
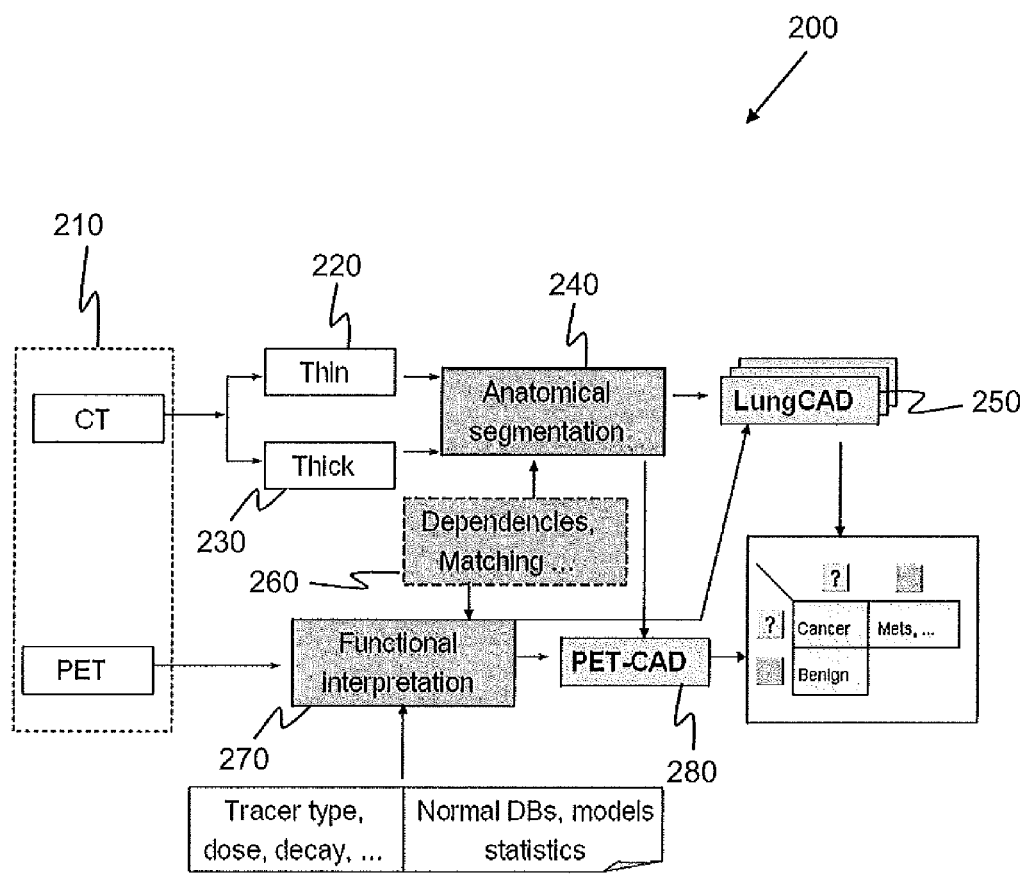
FIG. 2 illustrates a whole-body computer aided detection and diagnosis decision support system for oncology using PET/CT images, according to an exemplary embodiment of the present invention.

FIG. 2 illustrates a whole-body computer aided detection and diagnosis decision support system for oncology using PET/CT images, according to an exemplary embodiment of the present invention. As indicated by the dashed box labeled with reference numeral 210, the input to the system 200 is PET and CT scans of the whole body of a patient. For example, the CT scan may include thin slices 220 and/or thick slices 230.

The anatomical segmentation module 240 segments the CT images into anatomical organs, with labels for each. Each of the organs can be processed by an organ-specific CAD (computer aided detection/diagnosis) module 250, for example, LungCAD module. It is to be understood that the organ-specific CAD module 250 can be a colon CAD, cardiac CAD, etc.

The module 240 shown in FIG. 2 performs the linking between the CT and the PET data and the corresponding segmentation results. That is, the segmentation results for each data set are enhanced by using information coming from the other. The functional interpretation module 270 segments and interprets the PET image: where are the brains, and where is the bladder, etc., incorporating information from the scan itself, as well as information from learned models and statistics.

The PET-CAD module 280 performs lesion detection and characterization, incorporating information from the CT segmentation if available. The output of the organ CAD module and the PET-CAD module 280 is combined for an overall decision on the disease. Here, the output is shown as a decision for cancer staging. For example, is the lesion cancerous or benign; is it primary cancer, lymph node involvement, or metastasis?

Figure 3:
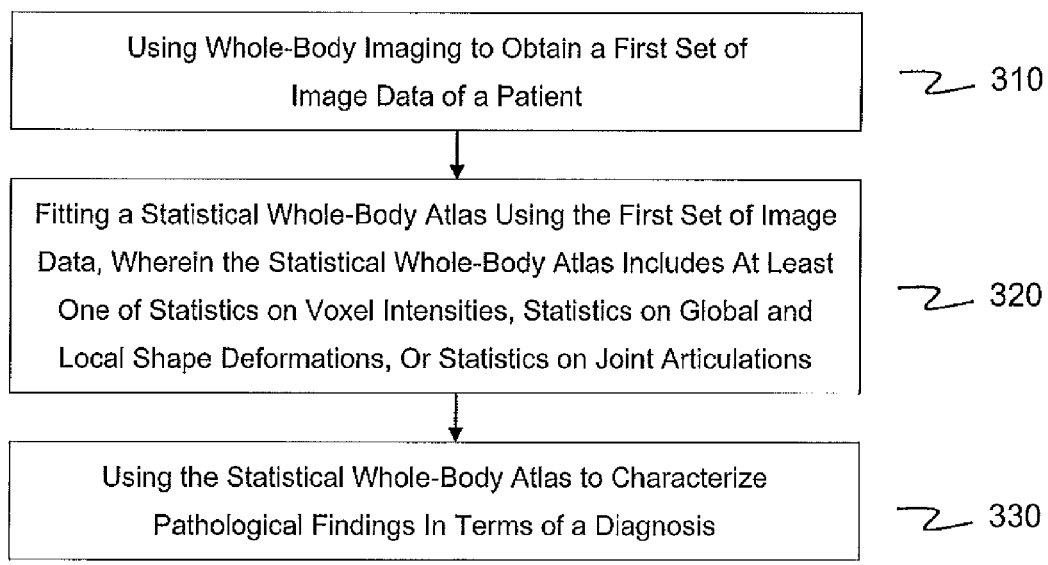
FIG. 3 is a flowchart showing a method of providing automatic diagnosis and decision support in whole-body imaging, according to an exemplary embodiment of the present invention.

FIG. 3 is a flowchart showing a method of providing automatic diagnosis and decision support in whole-body imaging, according to an exemplary embodiment of the present invention.

Referring to FIG. 3, in step 310, whole-body imaging is used to obtain a first set of image data of a patient.

The first set of image data is obtained using one or more imaging modalities. For example, the first set of image data may be obtained using whole-body positron emission tomography (PET) and one or more imaging modalities other than whole-body PET. For example, the first set of image data may be obtained using whole-body PET, CT, MRI, SPECT, PET/CT, SPECT/CT, and/or PET/MRI. The first set of image data may comprise 2-D image data, 3-D image data and/or higher-dimensional image data.

In step 320, a statistical whole-body atlas is fitted using the first set of image data. The statistical whole-body atlas includes statistics on voxel intensities, statistics on global and local shape deformations, and/or statistics on joint articulations. The statistical whole-body atlas may comprise distributional appearance models and/or spatial relational models of organs or structures in one or more whole-body imaging modalities.

In an exemplary embodiment of the present invention, the first set of image data includes PET data, and fitting the statistical whole-body atlas comprises automatically outlining selected regions of interest with pathological tracer uptakes while discounting physiological uptakes in the PET data. The first set of image data may include image data acquired by one or more imaging modalities other than PET. Using the statistical whole-body atlas to characterize pathological findings in terms of a diagnosis may comprise detecting anatomical or functional abnormalities of the whole body or body parts using the first set of image data.

Using the statistical whole-body atlas to characterize pathological findings in terms of a diagnosis may comprise automatically outlining selected regions of interest in the first set of image data and automatically extracting candidate features of interest from the selected regions of interest. Each of the candidate features of interest may be automatically contoured and characterized. For example, automatic contouring and characterizing may be based on standard uptake value and/or brain uptake normalized data.

In step 330, the statistical whole-body atlas is used to characterize pathological findings in terms of a diagnosis.

In an exemplary embodiment of the present invention, a method for providing automatic diagnosis and decision support in whole-body imaging further includes using whole-body imaging to obtain a second set of image data of the patient, using the whole-body atlas for pathological findings, and updating pathological findings based on the statistical whole-body atlas using the second set of image data. The second set of image data is obtained using one or more imaging modalities. For example, the second set of image data may be obtained using whole-body PET, CT, MRI, SPECT, PET/CT, SPECT/CT, and/or PET/MRI. Updating pathological findings based on the statistical whole-body atlas may comprise encoding anatomical or functional variations of the whole body or body parts using the second set of image data.

In an exemplary embodiment of the present invention, a method for providing automatic diagnosis and decision support in whole-body imaging further includes using whole-body imaging to obtain a third set of image data of the patient, using the whole-body atlas for pathological findings, and updating pathological findings based on the statistical whole-body atlas using the third set of image data. The third set of image data is obtained using one or more imaging modalities. For example, the third set of image data may be obtained using whole-body PET, CT, MRI, SPECT, PET/CT, SPECT/CT, and/or PET/MRI. Updating pathological findings based on the statistical whole-body atlas may comprise encoding anatomical or functional variations of the whole body or body parts using the third set of image data.

Figure 4:
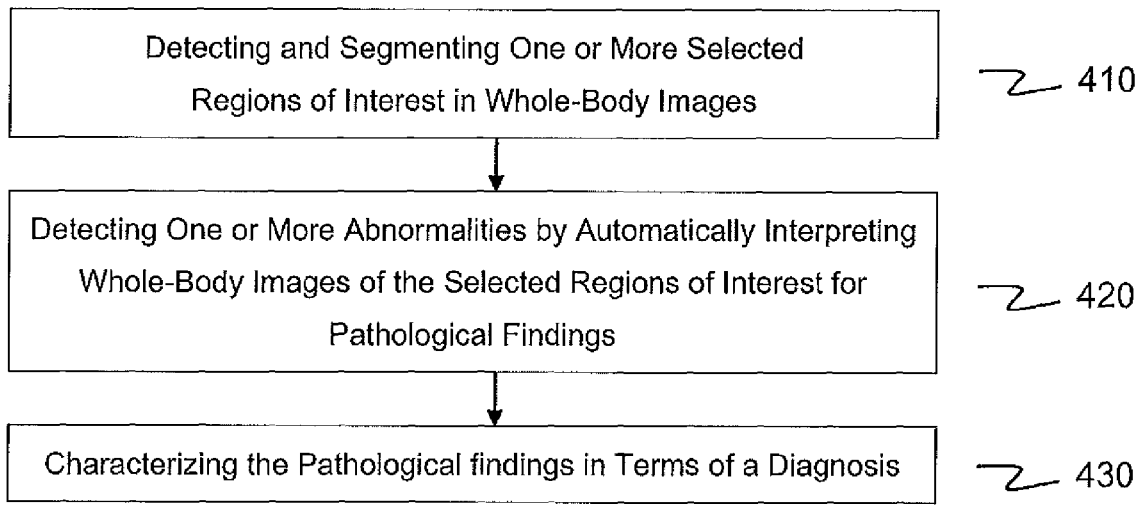
FIG. 4 is a flowchart showing a method of providing automatic diagnosis and decision support in whole-body imaging, according to an exemplary embodiment of the present invention.

FIG. 4 is a flowchart showing a method of providing automatic diagnosis and decision support in whole-body imaging, according to an exemplary embodiment of the present invention.

Referring to FIG. 4, in step 410, one or more selected regions of interest are detected and segmented. Segmenting the selected regions of interest may be accomplished using bounding boxes, centroid locations, bounding surfaces and/or a bounding mask. Segmenting the selected regions of interest may be automatically performed.

Although not shown in FIG. 4, a method of providing automatic diagnosis and decision support in whole-body imaging in accordance with an exemplary embodiment of the present invention may include detecting hotspots in the selected regions of interest from PET or SPECT images. The hotspots may be localized based on anatomical dependencies, and may be segmented using organ-specific thresholds. For example, to detect whole body metastatic spread in bones, one needs to see the bones first. To detect and characterize tumor involvement of lymph nodes, one may want to detect great vessels, since lymph nodes appear near these structures. In a general sense, CT in a PET/CT scan may be regarded as the source of anatomical context for functional hotspots revealed by PET.

In step 420, one or more abnormalities are detected by automatically interpreting whole-body images of the selected regions of interest for pathological findings. The whole-body images may be obtained using one or more imaging modalities. For example, the whole-body images may be obtained using whole-body PET, CT, MRI, SPECT, PET/CT, SPECT/CT, and/or PET/MRI. The selected regions of interest may comprise cells, tissues, organs and/or organ systems. For example, the selected regions of interest may comprise a liver, a lung or a kidney.

In step 430, the pathological findings are characterized in terms of a diagnosis. When longitudinal data is available, clinical analysis of the longitudinal data may be performed, and changes may be output in a clinically meaningful way. Since whole-body scans are often used for longitudinal studies, such as for example, oncology. Change quantification is useful during, for example, therapy response monitoring. Change quantification may be regarded as pattern detection in the context of time. Clinical priors or predispositions such as genetic predisposition are sometimes helpful for interpreting whole body images. For example, knowledge of the primary tumor location can help the assessment of regional lymph node involvement. For example, osteoarthritis will affect the PET uptake level in affected joints, menstruation cycle affects breast uptakes, and radiation therapy can result in elevated uptake levels in the axial skeleton and in neck fat.

It is to be understood that the present invention may be implemented in various forms of hardware, software, firmware, special purpose processors, or a combination thereof. In one embodiment, the present invention may be implemented in software as an application program tangibly embodied on a program storage device. The application program may be uploaded to, and executed by, a machine comprising any suitable architecture.

According to an exemplary embodiment of the present invention, there is provided a program storage device readable by machine, tangibly embodying a program of instructions executable by the machine to perform method steps for providing automatic diagnosis and decision support, the method steps comprising: using whole-body imaging to obtain a first set of image data of a patient; fitting a statistical whole-body atlas using the first set of image data, wherein the statistical whole-body atlas includes at least one of statistics on voxel intensities, statistics on global and local shape deformations, or statistics on joint articulations; and using the statistical whole-body atlas to characterize pathological findings in terms of a diagnosis.

According to an exemplary embodiment of the present invention, there is provided a program storage device readable by machine, tangibly embodying a program of instructions executable by the machine to perform method steps for providing automatic diagnosis and decision support, the method steps comprising: detecting and segmenting one or more selected regions of interest in whole-body images; detecting one or more abnormalities by automatically interpreting whole-body images of the selected regions of interest for pathological findings; and characterizing the pathological findings in terms of a diagnosis.

Although exemplary embodiments of the present invention have been described in detail with reference to the accompanying drawings for the purpose of illustration, it is to be understood that the inventive processes and systems are not to be construed as limited thereby. It will be readily apparent to those of reasonable skill in the art that various modifications to the foregoing exemplary embodiments may be made without departing from the scope of the invention as defined by the appended claims, with equivalents of the claims to be included therein.

What is claimed is:

1. A method for providing automatic diagnosis and decision support in whole-body imaging, comprising:
   using whole-body imaging to obtain a first set of image data of a patient;

detecting a plurality of anatomical landmarks in the first set of image data using a classification-based method;

fitting a statistical whole-body atlas using the first set of image data and the plurality of anatomical landmarks, wherein the statistical whole-body atlas encodes anatomical or functional variations of the whole-body or body parts and includes statistics on global and local shape deformations, and statistics on joint articulations; and using the statistics in the statistical whole-body atlas to characterize pathological findings in terms of a diagnosis, wherein the statistical whole-body atlas comprises at least one of mathematical distributional appearance models or spatial relational models of organs or structures in one or more whole-body imaging modalities, wherein the mathematical distributional appearance models or spatial relational models are learned based on annotated training data.

2. The method of claim 1, wherein the first set of image data is obtained using one or more imaging modalities.

3. The method of claim 1, wherein the first set of image data is obtained using whole-body positron emission tomography (PET) and one or more imaging modalities other than whole-body PET.

4. The method of claim 1, wherein the first set of image data includes PET data, and wherein fitting the statistical whole-body atlas comprises automatically outlining selected regions of interest with pathological tracer uptakes while discounting physiological uptakes in the PET data.

5. The method of claim 1, wherein the first set of image data further includes image data acquired by one or more imaging modalities other than PET, and wherein using the statistical whole-body atlas to characterize pathological findings in terms of a diagnosis comprises detecting anatomical or functional abnormalities of the whole body or body parts using the first set of image data.

6. The method of claim 1, wherein using the statistical whole-body atlas to characterize pathological findings in terms of a diagnosis comprises automatically outlining selected regions of interest in the first set of image data and automatically extracting candidate features of interest from the selected regions of interest.

7. The method of claim 6, wherein using the statistical whole-body atlas to characterize pathological findings in terms of a diagnosis further comprises automatically contouring and characterizing each of the candidate features of interest.

8. The method of claim 7, wherein automatic contouring and characterizing is based on at least one of a standard uptake value or brain uptake normalized data.

9. The method of claim 1, wherein the first set of image data comprises at least one of 2-D image data, 3-D image data or higher-dimensional image data.

10. The method of claim 1 further comprising:

using whole-body imaging to obtain a second set of image data of the patient; and updating pathological findings based on the statistical whole-body atlas using the second set of image data.

11. The method of claim 10, wherein updating pathological findings based on the statistical whole-body atlas comprises encoding anatomical or functional variations of the whole body or body parts using the second set of image data.

12. The method of claim 10 further comprising:

using whole-body imaging to obtain a third set of image data of the patient; and updating pathological findings based on the statistical whole-body atlas using the third set of image data.

13. The method of claim 12, wherein updating pathological findings based on the statistical whole-body atlas comprises encoding anatomical or functional variations of the whole body or body parts using the third set of image data.

14. A program storage device readable by machine, tangibly embodying a program of instructions executable by the machine to perform method steps for providing automatic diagnosis and decision support, the method steps comprising:

using whole-body imaging to obtain a first set of image data of a patient;

detecting a plurality of anatomical landmarks in the first set of image data using a classification-based method;

fitting a statistical whole-body atlas using the first set of image data and the plurality of anatomical landmarks, wherein the statistical whole-body atlas encodes anatomical or functional variations of the whole-body or body parts and includes statistics on global and local shape deformations, and statistics on joint articulations; and using the statistics in the statistical whole-body atlas to characterize pathological findings in terms of a diagnosis, wherein the statistical whole-body atlas comprises at least one of mathematical distributional appearance models or spatial relational models of organs or structures in one or more whole-body imaging modalities, wherein the mathematical distributional appearance models or spatial relational models are learned based on annotated training data.

15. The program storage device of claim 14 wherein the statistics on the global and local shape deformations include deformation fields or search ranges.

16. The program storage device of claim 14 wherein the statistics on the joint articulations include distributions of each joint articulation, means and variances of the joint articulations, or range of the joint articulations.

* * * * *